United States Patent [19]

Carney

[11] 4,351,345
[45] Sep. 28, 1982

[54] METHODS OF SECURING ELECTRODES TO THE HEART

[76] Inventor: Andrew L. Carney, 222 Forest Ave., Oak Park, Ill. 60302

[21] Appl. No.: 105,410

[22] Filed: Dec. 19, 1979

Related U.S. Application Data

[63] Continuation-in-part of Ser. No. 949,661, Oct. 10, 1978, abandoned.

[51] Int. Cl.³ ............................................ A61N 1/04
[52] U.S. Cl. ................................ 128/786; 128/419 P
[58] Field of Search ............. 128/419 P, 419 PG, 786

[56] References Cited

U.S. PATENT DOCUMENTS

| Re. 27,569 | 2/1973 | Ackerman | 128/419 P |
|---|---|---|---|
| 3,729,008 | 4/1973 | Berkevits | 128/419 P |
| 3,880,169 | 4/1975 | Starr et al. | 128/419 P |
| 3,952,742 | 4/1976 | Taylor | 128/419 P |
| 4,154,247 | 5/1979 | O'Neill | 128/419 P |
| 4,166,469 | 9/1979 | Littleford | 128/419 P |

*Primary Examiner*—William E. Kamm
*Attorney, Agent, or Firm*—Hume, Clement, Brinks, Willian & Olds, Ltd.

[57] ABSTRACT

A system for providing electrical stimulation to a heart muscle is especially characterized in that cardiac leads are passed through a surgically created opening in the wall of an atrium or the wall of a great vein adjacent an atrium into the interior of the heart. Procedures for placement of both atrial and ventricular cardiac leads are disclosed, which procedures can be used in connection with leads placed in both the left and right chambers of the heart. These procedures are especially suited for placing cardiac leads used with A-V sequential pacing, for they allow leads to be attached to both an atrium and a ventricle of a heart through a single small incision in the chest.

Improved cardiac leads are disclosed in which a channel is formed in the lead for receiving a guide probe such as tip manipulator or a malleable probe as an aid in lead placement. Other disclosed improvements relate to a spring clasp for securing an atrial lead to the atrial wall; a collar for assisting in securing a lead to the wall of a great vein or an atrium; position markers for leads; and an atrial lead having a barbed protruding element for passing through the atrial wall to secure the lead in place.

8 Claims, 11 Drawing Figures

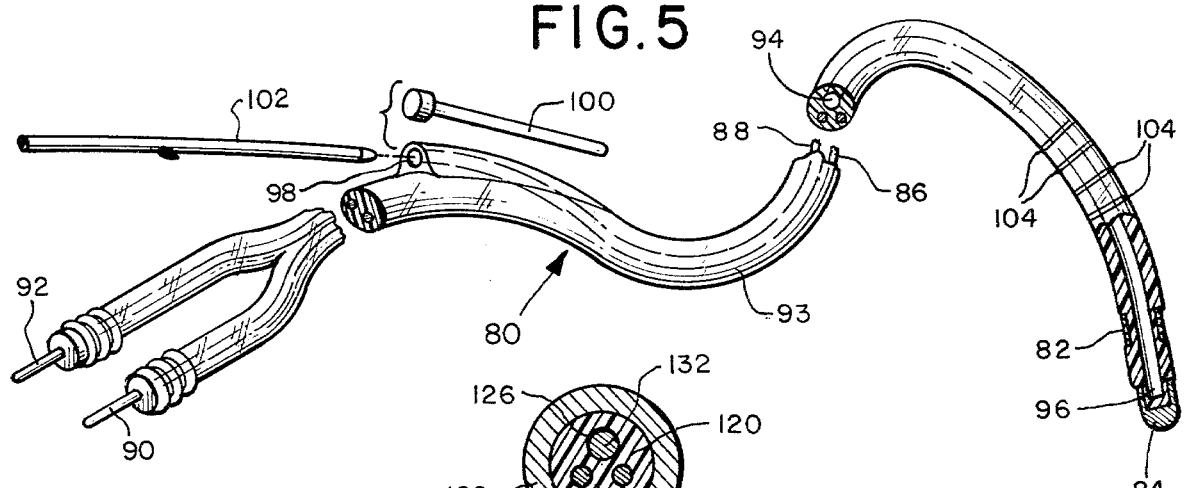
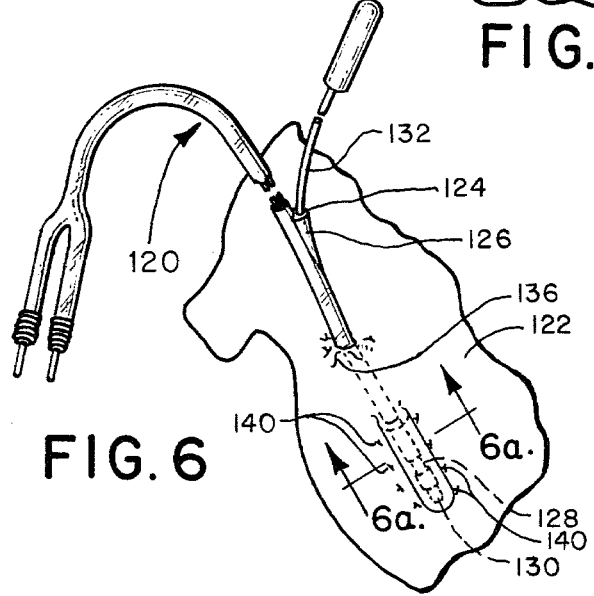
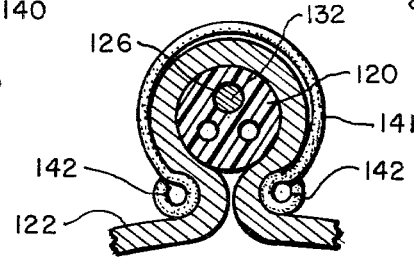
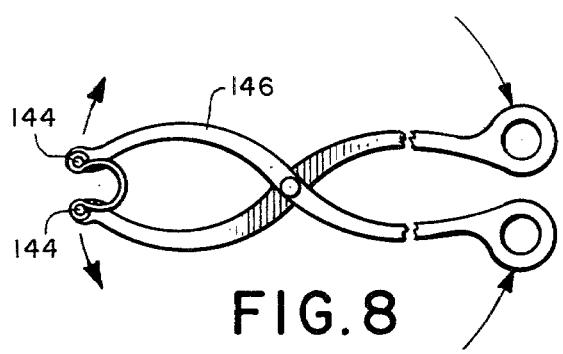
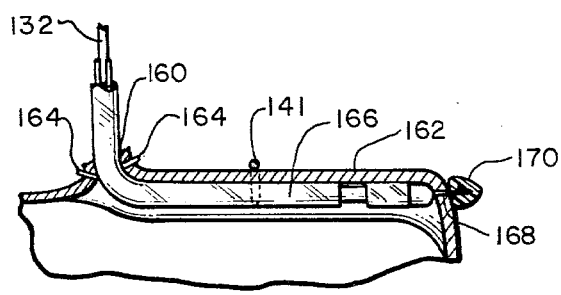
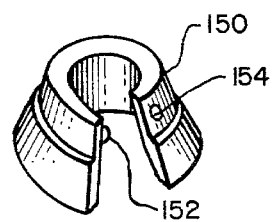

METHODS OF SECURING ELECTRODES TO THE HEART

This application is a continuation-in-part of earlier application Ser. No. 949,661, filed Oct. 10, 1978, now abandoned.

BACKGROUND OF THE INVENTION

This invention relates to a system for electrically stimulating the heart of a human or animal to improve the pumping action of the heart. The invention also relates to procedures and electrical leads for connecting a pulse generator (also referred to as a pacemaker or a cardiac stimulator) to a heart muscle. These procedures and leads permit a surgeon to implant electrical leads in both an atrium and ventricle of a heart through a single small incision in the chest.

The medical benefits of atrial-ventricular (A-V) sequential cardiac stimulation or pacing are well established. In A-V sequential pacing, electrical signals are applied to both atrial and ventricular regions of a heart muscle, and the two sets of signals are offset in time with respect to one another to produce properly sequenced electrical stimulation to the heart.

In spite of the recognized benefits of A-V sequential pacing, the use of this method of cardiac pacing has been somewhat limited by certain drawbacks. In the past, one important drawback has been that A-V sequential pacing requires that two sets of electrical leads be implanted in widely separated regions of the heart.

One method for implanting the two sets of leads is to open the chest in a formal thoracotomy. This method provides excellent access to the heart for lead placement, but the high surgical morbidity and mortality of formal thoracotomy is a severe drawback of the method. Patients with low cardiac reserve, who would most benefit from sequential pacing, would often not tolerate the proceedure.

A second approach for implanting the leads need for A-V sequential pacing is to introduce the leads transvenously into the heart. In this approach, leads are generally threaded through two blood vessels into the selected cardiac chambers.

In many cases, an atrial lead is passed transvenously into the atrium and is hooked in the atrial appendage. A ventricular lead is generally passed transvenously into the right atrium, through the tricuspid valve into the right ventricle. The transvenous approach to A-V sequential cardiac pacing generally requires the use of two veins and often difficult lead manipulation. Furthermore, proper atrial pacing is difficult to achieve with this approach, for the sensitivity of the atrium to electrical stimulation is not uniform and optimum atrial pacing can best be achieved by fixing the atrial electrode to that portion of the atrium most sensitive to stimulation. Patients subjected to previous cardiac surgery have greater difficulty with transvenous atrial pacing, because the loss of the atrial appendage makes the secure placement of the J-shaped electrodes almost impossible.

The transvenous approach avoids the high surgical morbidity and mortality of a formal thoracotomy. However, it brings with it other drawbacks. Undesired displacement of the lead is a common problem, and the optimal pacing site often cannot be selected because the lead cannot be secured to the appropriate portion of the atrial wall. Furthermore, there is an undesired incidence of perforation of the right ventricle with transvenous leads. This problem is exacerbated by the fact that it may be difficult to determine in positioning a transvenous lead whether resistance to lead movement is caused by impingement of the lead on the vessel wall or by the wall of the ventricle itself. Moreover, thrombosis of the subclavian vein has been reported in cases involving transvenous electrodes.

SUMMARY OF THE INVENTION

The present invention is directed to an improved system for providing electrical stimulation to a heart muscle. This system is well suited for use in A-V sequential pacing, for it overcomes many of these and other drawbacks of the prior art. The invention is also directed to improved cardiac electrical leads and improved procedures for implanting electrical leads in the heart.

According to this invention, access to the heart is gained by a small incision in the right parasternal region of the chest, an approach which provides good access to the right atrium as well as a portion of the left atrium. At least one cardiac lead is then secured to the heart transatrially, through an opening in the atrial wall. The atrial wall is punctured and the lead is passed through the puncture into the interior of the heart.

This technique may be used to position a ventricular lead by passing the lead from the atrium into the associated ventricle. Atrial leads can also be attached using this transatrial approach. Furthermore, leads can be positioned in either the right or left chambers of the heart according to whether the initial atrial puncture is made in the right or left atrium.

The right parasternal transatrial approach is well suited for A-V sequential pacing, for both atrial and ventricular leads can be implanted in the heat from a single small incision above the right atrium. Surgical access to the apex of the ventricle is not required, and a formal thoracotomy with its attendant drawbacks is avoided. Of course, the above-mentioned drawbacks of conventional transvenous cardiac leads are avoided as well.

The present invention also encompasses improved atrial and ventricular cardiac leads for transatrial implantation as well as means and procedures for securing a transatrial atrial lead to the atrial wall. These improvements are described in detail in the following detailed description.

The procedures and improvements of this invention offer several significant advantages over the prior art. As previously mentioned, both atrial and ventricular leads can be implanted through a single small thoracic incision, and important disadvantages of formal thoracotomies and transvenous approaches are thereby avoided. The improved cardiac leads of this invention can be positioned relatively easily, in that the surgeon has access to the surface of the heart. The improvements to the leads described below, such as position markers, means for receiving a guide means such as a guide probe, and means for securing the electrode to the heart wall, further facilitate lead placement and retention.

The invention, together with further objects and attendant advantages, will be best understood by reference to the following description taken in conjunction with the accompanying drawings.

BRIEF DESCRIPTION OF THE DRAWINGS

FIG. 5 is a perspective view of an improved bipolar ventricular lead.

FIG. 6 is a perspective view of a transatrial bipolar atrial lead secured adjacent an interior portion of the atrial wall.

FIG. 6a is a cross-sectional view of the atrial lead of FIG. 6 secured adjacent an interior portion of the atrial wall.

FIG. 7 is a cross-sectional view similar to that of FIG. 6a showing a spring clasp for securing the lead in place adjacent the atrial wall.

FIG. 8 is a plan view of the spring clasp of FIG. 7 and an applicator.

FIG. 9 is a perspective view of a collar used in securing a transatrial ventricular lead to the atrial wall.

FIG. 10 is a sectional view of a second transatrial atrial lead secured to the atrial wall.

DETAILED DESCRIPTION OF PREFERRED EMBODIMENTS

The following discussion treats several preferred embodiments of the system, procedures and cardiac leads of the present invention. One of the important advantages of this invention is that it permits all the electrical leads needed for A-V sequential pacing to be secured to the heart through a single, small incision in the chest. FIGS. 1-4 represent a preferred embodiment of the invention in which atrial and ventricular leads are positioned in a surgical procedure which can be done under local anesthesia in some patients.

Figure 1:
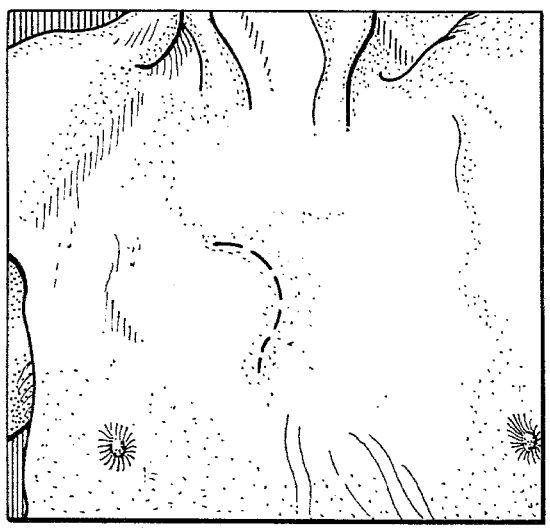
FIG. 1 represents the size and location of a right parasternal incision through which A-V sequential pacing leads have been implanted in the heart of a male patient in a preferred embodiment of the system of this invention.

In this preferred embodiment the right atrium is approached through a convex, right parasternal incision over the third costal cartilage. As shown in FIG. 1, this incision is relatively small, measuring approximately 6 to 8 centimeters in length in male patients. Following the incision, the third costal cartilage is resected. The pericardium is then mobilized and incised longitudinally with stay sutures applied for traction.

Excellent exposure of the right atrium is obtained by this approach. The superior vena cava and the sinus bearing atrium are readily accessible, as are the lateral the thicker medial atrial walls. The surgical procedures used to access the heart by resecting costal cartilage are known and need not be described in any detail here. See, e.g. James W. Calvin, "Permanent Atrial Pacing," *Archives of Surgery* 111, pp. 712-715 (June, 1976). However, these procedures have in the past been used to gain access to the heart through the bed of the fourth costal cartilege. To applicant's knowledge, access via the bed of the third costal cartilege is a novel procedure which provides improved exposure of the right atrium in most cases. In a tall individual having a low lying heart, access through the bed of the fourth costal cartilege may be preferred.

Once the right atrium is exposed, cardiac leads are placed in the heart. Various types of cardiac leads can be used; the following procedure utilizes two pinch-on type atrial leads and a transvenous type ventricular lead.

Figure 2:
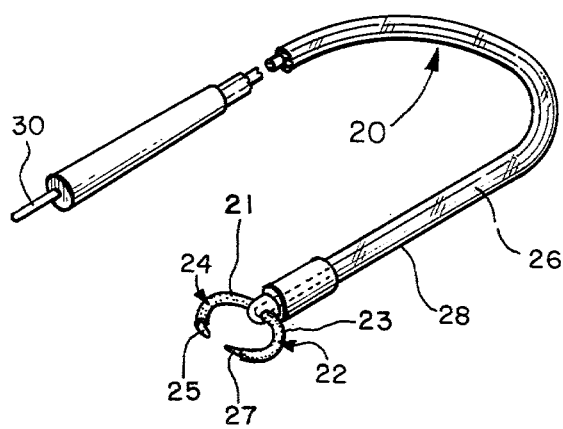
FIG. 2 is a perspective view of a portion of a conventional pinch-on atrial lead.

A pinch-on type atrial lead 20, as shown in FIG. 2, includes a pair of partially insulated deformable opposed tips 22,24 which are electrically connected to an electrical conductor 26 insulated by a sleeve 28. Insulating sheaths 21,23 insulate all but the bare electrodes 25,27 of the tips 22,24. The conductor 26 terminates in a connector plug 30 which is sized to mate with the output socket of a pulse generator. A suitable pinch-on lead is manufactured by Medtronic, Inc., and is identified as a Myocardial Atrial Pinch-On Lead (Medtronic Model No. 6995).

Figure 3:
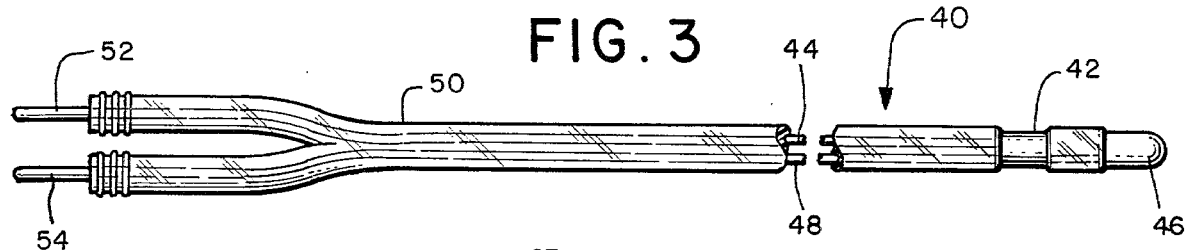
FIG. 3 is a plan view of a portion of a conventional bipolar transvenous ventricular lead.

A transvenous bipolar, ventricular lead used in this embodiment, as shown in FIG. 3, has first and second electrodes 42,46 coupled to first and second isolated electrical conductors 44,48, respectively. The lead 40 is provided with a layer 50 of flexible insulating material and includes conductor plugs 52,54 for connecting the lead to a pulse generator. A suitable lead is manufactured by Medtronic, Inc., and is identified as a Transvenous Endocardial Lead (Medtronic Model No. 6902).

Figure 4:
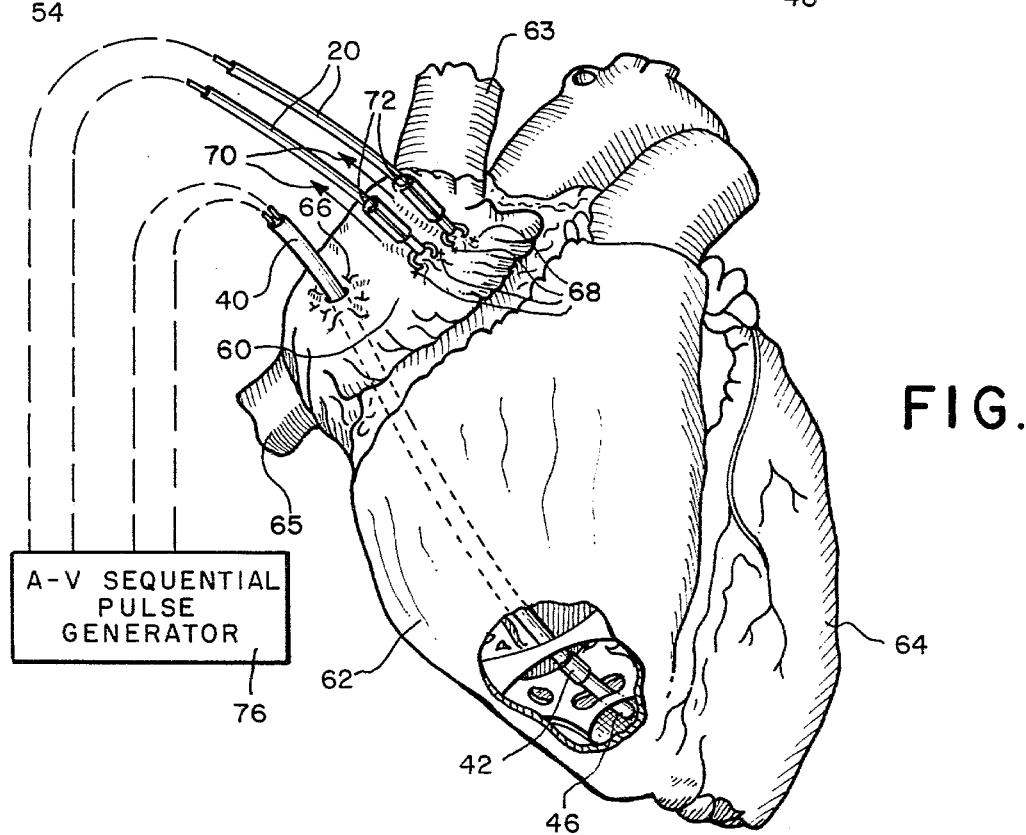
FIG. 4 is a perspective view of an isolated heart showing a preferred transatrial placement of the ventricular lead and exemplary placement of the atrial leads.

The method of attaching the electrodes 20,40 to the heart will be explained in conjunction with FIG. 4, which shows a perspective view of an isolated heart, including portions of the surface of the right atrium 60, the right ventricle 62, the left ventricle 64, the superior vena cava 63, and the inferior vena cava 65. It should be understood that in the right parasternal approach described above, it is primarily the surface of the right atrium which is exposed, and the heart is much less accessible than as shown in FIG. 4.

The general method for attaching pinch-on leads 20 to the atrium is well known. Briefly, the method involves fitting the tips 22,24 into a plastic applicator (not shown), and then using a surgical clamp (not shown) to deform the applicator and the tips 22,24, to close the tips 22,24 into a circular configuration. The tips are positioned adjacent a fold in the atrial wall so that the tips 22,24 pierce the atrial wall as they are closed, thereby securing the lead to the atrium and establishing electrical contact between the electrodes 25,27 and the atrium. See, e.g., "Permanent Atrial Pacing," supra, and references cited therein.

An important advantage of the procedure of this invention is that it permits good access to the right atrium, which permits the attachment point for the atrial electrode to be freely selected. Preferably, this improved exposure of the atrium should be utilized to achieve optimum lead placement. The atrial surface can be mapped to determine that portion which has the lowest stimulation threshold, and then the atrial lead can be attached at this point. Very commonly, the medial inferior aspect of the atrium has the lowest threshold and the sinus node has the highest threshold.

As an improvement to this general method of securing pinch-on leads, the applicant has developed a two-point attachment for pinch-on leads which reduces the tendency of the pinch-on electrodes 25,27 to continuously slide and reorient themselves in the atrial wall. Such reorientation, if not restrained, may allow the electrodes 25,27 to move out of electrical contact with the heart, thereby interrupting cardiac pacing. In applying this two point attachment, a horizontal mattress stitch 68 is used to create a ridge in the atrial wall. The ridge is further defined by traction parallel to the ridge in the direction of the arrows 70. The pinch-on lead is then applied to the ridge. The body of the lead is then attached to the ridge by sutures 72 to complete the two point attachment.

The method for attaching the venticular lead requires exposure of the atrium only. First a purse string suture 66 is placed on the lateral aspect of the right atrium near the septum and a tourniquet (not shown) is applied. Then a stab wound is made in the atrial wall within the purse string suture 66 and the ventricular lead 40 is introduced through the wound into the interior of the atrium. In order to reduce movement of the ventricular lead, the purse string suture 66 and the stab wound are preferably placed to avoid areas of marked atrial movement. The tourniquet is used to press the atrial wall against the lead 40 to reduce blood flow out of the heart and to secure the lead to the heart during placement.

The ventricular lead 40 may be positioned near the apex of the right ventricle in the conventional manner. Preferably an image amplifier is used to aid in guiding the lead through the tricuspid valve into the right ventricle. The electrodes 42,46 should preferably be positioned in the same part of the ventricle as with conventional transvenous ventricular leads.

After the ventricular lead 40 has been properly positioned the lead 40 is secured to the atrial wall, as for example, by tieing a heavy silk suture around the lead and the proximal portion of the atrial wall, before the tourniquet is loosened. This reduces the tendency of the lead to shift position. The leads 20,40 are then routed and connected to a pulse generator 76 and the chest is closed in the conventional manner.

The foregoing system and procedure have been successfully used to implant conventional leads for A-V sequential pacing in human subjects. However, it should be understood that the invention encompasses various transatrial electrodes and procedures for their use and is not limited to the embodiments described above. For example, the transatrial approach of this invention can be used to implant leads in the left as well as the right atrium and ventricle, and it can be used with other leads than those discussed above. The following discussion describes improved leads and procedures for transatrial introduction of leads into the heart.

FIG. 5 shows an improved bipolar ventricular lead 80 which is similar in many respects to the lead 40 of FIG. 3. Lead 80 includes electrodes 82,84 which are connected to connector plugs 90,92 by electrical conductors 86,88. A flexible insulating sheath 93 covers the conductors 86,88. These elements of the lead 80 can be constructed out of the same materials as previously described lead 40.

The principal improvement of the electrode 80 is a tunnel-like channel 94 which extends along almost half the length of the lead 80 from an opening 98 near the midpoint of the lead to a termination point 96 near the electrode 84. This channel 94 is formed in the insulating sheath 93 and is sized to receive guide means such as a guide probe 102 having a tip manipulator.

Guide probes having tip manipulators are well known in the surgical art. Such probes are widely used in conjunction with catheter placement, where they are used to remotely control the configuration and orientation of the distal end of the catheter. Several manufacturers, including Cook Inc., (P.O. 489, Bloomington, Ind. 47401) currently market catheter tip manipulators.

The lead 80 is used by inserting a guide means such as a guide probe 102 having a tip manipulator into the opening 98 in the channel 94. The tip of the guide probe is placed near the termination point 96 of the channel 94. In general, better lead control is provided with shorter, larger diameter guide probes, and the size of the guide probe should be chosen to fit the intended application. For example, catheter tip manipulators are currently made with diameters of both 0.052" and 0.098", and either may be used in conjunction with the lead 80. In all cases the diameter of the channel 94 should be somewhat larger than the diameter of the tip manipulator to ensure that the tip manipulator can be easily removed from the lead 80 without undue friction following lead placement. In that this approach permits access to the surface of the heart, the opening 98 can be placed nearer the tip 96 than in conventional transvenous electrodes. This permits the use of shorter and more controllable tip manipulators.

The guide probe is used to direct the lead 80 to achieve proper placement. Once proper placement has been achieved, the guide probe is removed and the opening 98 is capped with a pin 100. The pin 100 is preferably made of a material such as Teflon, a registered trademark and is used to prevent tissue from entering and blocking the opening 98 in the implanted electrode. The channel 94 can be reopened by simply removing the pin 100, if needed for repositioning of the lead at a later time. Alternate embodiments may provide a channel 94 which is formed by a sleeve separate from the lead 80 in the region near the opening 98. This sleeve may be simply tied off in order to seal out body tissue. Lead 80 is especially useful as a left ventricular transatrial lead, because the left atrium and ventricle are less exposed than the right atrium and ventricle in the right parasternal approach, and increased control over lead movement will, therefore, be preferable.

One method of constructing guide probes having tip manipulators such as those referred to above is to run a number of separate flexible control leads or wires from the proximal to the distal ends of the probe. Then, by selectively altering the differential lengths of the control leads, the orientation and configuration of the distal end of the probe can be controlled. Alternate embodiments of the lead 80 may use the conductors 86,88 themselves both as control leads for the tip manipulator and electrical conductors for the electrodes. Such integration of the tip manipulator into the structure of the lead might well result in a lead having a smaller diameter than otherwise.

A further noval feature of this embodiment of the lead 80 is that it is provided with position markers, such as a series of visible rings 104. These position markers are used to aid in properly positioning the lead 80 in the ventricle. For example, once the lead 80 is properly positioned, with the aid of an image amplifier, for instance, the position of the lead 80 can readily be noted by observing the markers 104. Then, if the lead 80 shifts during the final stages of implanting the lead, it can readily be returned to the desired position.

FIG. 9 shows a preferred embodiment of an anchor member such as a collar 150 which serves as an aid in securing the lead 80 to the atrial wall near the stab wound. The collar 150 includes a locking pin 152 and a mating socket 154. Preferably the collar 150 is made of a nontoxic material such as silicone rubber. In use, the collar 150 is installed on the lead 80 after the lead has been implanted in the heart by positioning the collar 150 around the lead 80 near the point where the lead 80 enters the atrium, and then locking the collar in place by inserting the pin 152 into the socket 154. The collar 150 serves as an aid in positioning and securing the lead 80, for it serves to mark a selected point on the lead. It also provides an anchor point on the lead which is used as a tiedown in suturing the lead to the atrial wall adjacent the stab wound.

A preferred embodiment of a trans atrial atrial lead 120 is shown implanted in a heart in FIGS. 6 and 6a, where the lead 120 is shown secured to the medial inferior wall 122 of the right atrium. This lead 120 is similar to the previously described lead 80 in many respects. The principal difference between the two is that the opening 124 in the channel 126 is placed within 2–4 inches of the electrodes 128,130. Because this atrial lead will be secured to the atrail wall 122 (as described below), it is less likely that repositioning of the lead will be required. The channel opening 124 can, therefore, be placed nearer the electrode in order to shorten the channel 126 and increase control over lead position. Guide means such as a malleable probe 132 is preferably used with the lead 120 to provide rigidity during placement of the lead 120.

The lead 120 is implanted through a procedure which is in many ways similar to the previously described procedure for trans atrial placement of ventricular electrodes. As before, access to the right atrium is preferably gained by resecting the third costal cartilage and the lead is introduced through a surgically created opening in the atrial wall. In this case, a stab wound is placed through a purse string in the right atrium in such a manner that the tip of the lead can be positioned to contact that portion of the atrium having the lowest stimulation threshold. Purse string sutures 136 are used to close the stab wound about the lead 120.

Once the tip of the lead 120 is inserted into the atrium, the lead is secured adjacent the interior surface of the atrial wall by horizontal mattress stitches 140. As best shown in FIG. 6a the lead 120 is captured in a fold of the atrial wall 122 by the stitches 140, thereby insuring good electrical contact between the electrodes 128,130 and the atrial wall as well as retention of the lead.

FIGS. 7 and 8 show a preferred embodiment of a spring clasp which can be used instead of mattress stiches 140 to hold the trans atrial atrial lead 120 in place. In this preferred embodiment, a spring clasp 141 is used which is made of a spring material which is either itself nontoxic or is coated with a material which is nontoxic. For example, the clasp 141 is preferably made from a piece of spring wire having a substantially circular cross section which is covered with silicone rubber plastic or teflon. The clasp 141 as shown in FIG. 7 is substantially in its rest, or relaxed, position. In order to install the clasp 141, it is opened to slip over the lead 120 and the folded atrial wall 122. Then, when released, the clasp 141 resiliently returns to the position of FIG. 7, thereby securing the lead 120 in place. The clasp 141 is provided with a pair of openings 142. These openings 142 are sized to slip over mating pins 144 on an applicator 146 which is used to open the spring clasp 141 for insertion around the lead 120. A preferred embodiment of the applicator 146 is shown in FIG. 8.

A second method of securing a transatrial lead to the atrial wall is shown in FIG. 10. Once again the lead is passed through a stab wound 160 in the right atrium which permits optimum placement of the electrode against the atrial wall. As before, purse string sutures 164 close the wound 160 about the lead 166. In this embodiment the bipolar lead 166 is provided with a channel for receiving a malleable probe 132. The lead 166 is provided with piercing means such as a barbed protruding element 168 which is used to secure the tip of the lead to the atrial wall. A cap 170 is pressed onto the barbed element 168 from the outside of the heart to firmly secure the lead 166 to the heart. Preferably, the lead is also attached to the atrial wall at least one other point, as, for example, by means of a spring clasp 141 as shown in FIG. 9 or a horizontal mattress stitch.

It has been found that under certain circumstances it is preferable to insert atrial or ventricular leads through a surgically created opening in the superior vena cava rather than the atrial wall. This is particularly the case where the atrial wall is thin or friable, or otherwise easily damaged, for in these cases an undesirable amount of leakage through the atrial wall around the lead can result. Furthermore, a reduced incidence of post operative cardiac disrythmia has been observed in connection with cardiac leads inserted through the superior vena cava as compared with the atrial wall.

The procedures used to insert leads through the superior vena cava are quite similar to those described above. Access to the heart is preferably gained through the third intercostal space. A purse string suture is placed around a portion of the anterior aspect of the superior vena cava, preferably within about three centimeters of the junction between the superior vena cava and the atrium. A tourniquet is then applied to the purse string suture and a stab wound is made in the wall of the superior vena cava, within the suture. A lead as described above is then inserted into the superior vena cava and into the atrium itself. The tourniquet is used to press the wall of the superior vena cava against the lead to reduce blood flow around the lead and to secure the lead during placement. If the lead is a ventricular lead, it is pushed through the atrium into the ventricle. Each of the leads and methods of lead insertion and attachment described above can be used in connection with the approach.

Similarly, leads can be introduced into either or both the left atrium and the left ventrical through a surgically created opening in the superior pulmonary vein near the point at which the vein enters the left atrium. In the following claims, the terms "great vein" will be used generically to include both the superior vena cava and pulmonary vein.

From the foregoing discussion it should be apparent that the present invention is directed to a system for A-V sequential pacing as well as procedures for transatrially securing permanent leads to the heart and improved transatrial leads. The procedure is a flexible one through which atrial and ventricular leads can be implanted in either the right or left sides of the heart through a small incision. The procedure permits a simple approach to A-V sequential pacing.

Of course, it should be understood that various changes and modifications to the preferred systems, procedures, and embodiments described herein will be apparent to those skilled in the art. For example, monopolar electrodes, as well as bipolar electrodes, can be used in this invention. Such changes and modifications can be made without departing from the scope of the present invention and without diminishing its attendant advantages. It is, therefore, intended that such changes and modifications be covered by the following claims.

I claim:

1. A method for securing cardiac leads to a heart which includes a ventricle which is in fluid communication with an associated atrium via a valve, said method comprising the following steps:

providing an atrial-ventricular pulse generator having an atrial lead and a ventricular lead;

gaining access to the atrium;

securing the atrial lead to the atrium to provide electrical contact between the pulse generator and the atrium via the atrial lead;

sugically creating an opening in the atrium;

passing the ventricular lead through the surgically created opening into the atrium, through the valve and into the ventricle to provide electrical contact between the ventricle and the pulse generator via the ventricular lead; and closing the surgically created opening around the ventricular lead to secure the ventricular lead in place and to substantially prevent the leakage of blood out of the atrium around the ventricular lead.

2. The invention of claim 1 further comprising the step of securing the ventricular lead to the atrium adjacent the surgically created opening by means of sutures.

3. A method for securing cardiac leads to a heart which includes a ventricle which is in fluid communication with an associated atrium via a valve, said method comprising the following steps:

providing an atrial-ventricular pulse generator having an atrial lead and a ventricular lead;

gaining access to the atrium and to a great vein which supplies blood to the atrium;

securing the atrial lead to the atrium to provide electrical contact between the pulse generator and the atrium via the atrial lead;

surgically creating an opening in the great vein at a point near the atrium;

passing the ventricular lead through the surgically created opening into the atrium, through the valve and into the ventricle to provide electrical contact between the ventricle and the pulse generator via the ventricular lead; and closing the surgically created opening around the ventricular lead to secure the ventricular lead in place and to substantially prevent the leakage of blood out of the great vein around the ventricular lead.

4. The invention of claim 3 wherein the surgically created opening in the great vein is placed within about three centimeters of the atrium.

5. The invention of claim 1 or 3 wherein the ventricular lead defines a channel sized to receive a guide probe.

6. The invention of claim 1 or 3 further comprising a plurality of position markers spaced along a portion of the ventricular lead.

7. The invention of claim 1 or 3 wherein access to the atrium is gained through the bed of the third costal cartilege.

8. The invention of claim 1 or 3 wherein the ventricular lead is positioned with an end of the ventricular lead near the apex of the ventricle.

* * * * *